US005639462A

United States Patent [19]

MacAdam et al.

[11] Patent Number: 5,639,462
[45] Date of Patent: Jun. 17, 1997

[54] ATTENUATED POLYIVIRUSES VACCINE CONTAINING THEM AND VACCINATION METHODS USING THEM

[75] Inventors: Andrew Joseph MacAdam; Philip David Minor, both of Potters Bar; David Michael Stone; Jeffrey William Almond, both of Reading, all of United Kingdom

[73] Assignee: British Technology Group Limited, London, England

[21] Appl. No.: 239,858

[22] Filed: May 9, 1994

Related U.S. Application Data

[63] Continuation of Ser. No. 60,510, May 12, 1993, abandoned, which is a continuation of Ser. No. 697,347, May 9, 1991, abandoned.

[30] Foreign Application Priority Data

Apr. 10, 1991 [GB] United Kingdom .................. 9107552

[51] Int. Cl.$^6$ .............................. C12N 7/01; C12N 15/43

[52] U.S. Cl. .................. 424/217.1; 424/93.6; 435/235.1; 435/236; 435/172.3

[58] Field of Search .............................. 424/217.1, 172.3; 435/235.1, 236

[56] References Cited

FOREIGN PATENT DOCUMENTS

| | | |
|---|---|---|
| 0323900 | 1/1989 | European Pat. Off. . |
| 0325768 | 12/1989 | European Pat. Off. . |
| 0383434 | 8/1990 | European Pat. Off. . |
| 0383433 | 8/1990 | European Pat. Off. . |
| 9008189 | 7/1990 | WIPO . |

OTHER PUBLICATIONS

P.D. Minor et al. "The effect of sequences in the 5'. . . " J. Gen. Virol. (1988) 69, pp. 1091–1096.

L. Stanway et al. "Comparison of the complete . . . " Proc. Natl. Acad. -Sci. 81 (Mar. 1984), pp. 1539–1543.

A.Z. Zelent et al. "Replicative Intermediate of . . . " J. Virol., 1987), (Sep. 1987), pp. 2921–2923.

G. Stanway et al. "Construction of poliovirus intertypic . . . " Jour of Virology, vol. 57 No. 3 (Mar. 1986), pp. 1187–1190.

Evans et al "Increased Neurovirulence . . . " Nature vol. 314, Apr. 11, 1985, 548–550.

Toyoda et al "Complete Nucleotide Sequences . . . " Jour. of Mol. Biology, vol. 124, 1984, pp. 263–270.

Biological Abstracts No. 73356 vol. 88 No. 7 1989 pp. AB–392.

Chemical Abstracts No. 228104s, vol. 109, No. 25 19 Dec. 1988, p. 614.

Chemical Abstracts No. 118401g, vol. 114, No. 13, 1 Apr. 1991, p. 414.

Nomoto et al "Complete Nucleotide . . ." Proc. of Natl Aca of Sciences vol. 79, Oct. 1982, pp. 5793–5797.

E.V. Pilipenko et al., Virology 169, 201–209 (1989) "Conserved Structural . . . ".

R. Ren, et al., J. of Virology, Mar. 1991, 1377–1382 "Identification of Two . . . ".

S. Kuge, et al., J. of Virology, May 1987 1478–1487 "Construction of Viable . . . ".

P.D. Minor, et al., J. Gen. Virol. (1988) 69, 1091–1096, "The Effect of Sequences . . . ".

J. Pelletier, et al., J. of Virology, Dec. 1988 pp. 4486–4492 "Mutational Analysis . . . ".

S. Van Der Werf, et al., Proc. Natl. Acad. Sci. USA. vol. 83 pp. 2330–2334, Apr. 1986.

V.M. Rivera, et al., Virology 165, 42–50 (1988) "Comparative Sequence . . . ".

N. La Monica, et al., J. of Virology, Feb. 1986 pp. 515–525 vol. 57 No. 2 "Mapping of Sequences Required For Mouse . . . ".

Y.V. Svitkin, et al., Virology 166, 394–404 (1988) "Point Mutations . . . ".

A.J. Cann, et al., Nucleic Acids Research vol. 12, No. 30, 1984 1787–1792 "Revision to . . . ".

G. Stanway, et al., vol. 11, No. 16 1983, Nucleic Acids Research pp. 5629–5643 "The Nucleotide Sequence of Poliovirus . . . ".

Nomoto et al. Positive Strand RNA Viruses pp. 437–452 1987 UCLA Symp. Mol. Cell. Biol. (New Series) 54 Ed. M.A. Brinton.

A.J. Macadam, et al., Virology 181, 451–458 (1991) "The 5'noncoding region . . . ".
Biochem Genetics vol. 108 (1987) 144367 w. J.W. Almond et al., J. of Virological Methods 17 (1987) 183–189 "Studies . . . ".
JP-A-60207582 (Nihon Porio Kenkyscho) Abstract vol. 10 No. 67, (C-333) (2124) Mar. 15, 1986.
Almond et al. J. Virol. Meth, vol. 17 (1–2) (1987) pp. 183–189.
La Monica et al J. Virol. vol. 61(9) (1987) pp. 2917–2920.
Gillis DeWalt et al J. Virol. vol 61(7) (1987) pp. 2162–2170.
Skinner, M.A. et al (1989) J. Mol. Biol. 207:379–392.

*Primary Examiner*—Lila Feisee
*Assistant Examiner*—Julie E. Reeves
*Attorney, Agent, or Firm*—Nixon & Vanderhye

[57] ABSTRACT

An attenuated poliovirus in which the 5' non-coding region of the genome is:

(a) the 5' non-coding region of poliovirus type 3 Leon strain modified by the provision of the bases uracil and adenine at positions 472 and 537 thereof respectively, or (b) the 5' non-coding region of another poliovirus modified by the provision of the bases uracil and adenine at respective positions corresponding to position 472 and 537 of the 5' non-coding region of poliovirus type 3 Leon strain.

19 Claims, No Drawings ize>ATTENUATED POLYIVIRUSES VACCINE CONTAINING THEM AND VACCINATION METHODS USING THEM This is a Continuation of application Ser. No. 08/060,510, filed May 12, 1993, now abandoned, which is a Continuation of application Ser. No. 07/697,347, filed May 9, 1991, now abandoned.

This invention relates to the construction of vaccines against polioviruses, by the introduction of defined mutations into their genomes. These mutations attenuate the virulence of wild type viruses and can further attenuate existing live attenuated vaccine virus strains, thereby making them less likely to revert to virulence.

At the present time, the only vaccines routinely used against enterovirus and rhinovirus infections are those against poliomyelitis. Of these the live attenuated vaccines developed by Sabin in the 1950's have found greatest use throughout the world. Vaccine strains derived from each of the three poliovirus serotypes (P1, P2 and P3) were prepared by passage of wild type viruses in cell cultures and whole animals until attenuated strains were obtained. These attenuated viruses are substantially less able to cause poliomyelitis in humans than the original wild type strains. They are administered orally and replicate in the gut to induce a protective immune response.

Although these vaccines are generally regarded as safe, their use is associated with a low level of paralysis in vaccinees. This is most often associated with type 2 and type 3 serotypes and rarely, if ever, with type 1. There is therefore a requirement for improved type 2 and type 3 vaccines which would be comparable in safety to the excellent type 1 strain.

The Sabin vaccine strains were developed by essentially empirical procedures. The genetic basis of their attenuation is not properly understood. Over the past few years, however, scientists have employed a number of molecular biological techniques in an attempt to elucidate the mechanism by which the neurovirulence of these vaccine strains is reduced. Most of the work has concentrated on serotypes 1 and 3. For both of these the complete nucleotide sequences of the vaccine strains have been compared with those of their neurovirulent progenitors.

In the case of poliovirus type 1, the vaccine strain differs from its progenitor at 57 positions in the 7441 base genome (Nomoto et al, 1982, *Proc Natl Acad Sci USA* 79:5793–5797). All of these are simple point mutations and 21 of them give rise to amino acid changes in virus coded proteins. Although several mutations are thought to contribute to the attenuation phenotype of the vaccine strain, direct evidence has been presented that the mutation of A to G at position 480 in the 5' non-coding region of the genome has a marked attenuating effect on the virus (Nomoto et al, 1987, UCLA *Symp Mol Cell Biol*, New Series, Vol 54 (Eds M. A. Brinton and R. R. Rueckert), 437–452, New York: Alan R Liss Inc).

Analogous studies on poliovirus type 3 reveal just 10 nucleotide sequence differences in the 7432 base genome between the vaccine and its progenitor strain (Stanway et al, 1984, *Proc Natl Acad Sci USA* 81:1539–1543). Just three of these give rise to amino acid substitutions in virus encoded proteins. The construction of defined recombinants between the vaccine and its progenitor strain has allowed the identification of the mutations which contribute to the attenuation phenotype. One of these is at position 2034 and causes a serine to phenylalanine change in virus protein VP3.

The other mutation of interest is C to U at position 472 in the 5' non-coding region of the genome. This latter mutation has been observed to revert to the wild type C rapidly upon replication of the virus in the human gut (Evans et al, 1985, *Nature* 314:548–550). This reversion is associated with an increase in neurovirulence. C at position 472 has also been shown to be essential for growth of a mouse/human polio recombinant virus in the mouse brain (La Monica et al, 1986, *J Virol* 57:515–525). Recently, we have observed that at 481 in poliovirus type 2 A changes to G in an analogous fashion upon replication of the type 2 vaccine in the gut of vaccinees.

In EP-A-0383433 attenuated enteroviruses, particularly polioviruses, and rhinoviruses are described which have a reversed base pairing in the part, or in a part corresponding to the part, of the 5' non-coding region of the genome of poliovirus type 3 Leon strain shown below:

| 471 | 477 | 483 |
|---|---|---|
| ...UCC.... | CCAUCGA.... | |
| ...AGG.... | GGUGCCU.... | |
| 538 | 534 | 528 |

EP-A-0383433 indicates that a suitable attenuated poliovirus of type 1 or type 2 has the bases G and C at positions 469 and 534 respectively and that a suitable attenuated poliovirus of type 3 has the bases G and C at positions 472 and 537 respectively.

We have now constructed a type 3 poliovirus in which the bases at positions 472 and 537 of the genome are uracil (U) and adenine (A) respectively. This poliovirus is more attenuated than an attenuated type 3 poliovirus according to EP-A-0383433 but less attenuated than the Sabin vaccine strain of type 3 poliovirus. The type 3 Sabin strain alters rapidly as it grows in the intestinal tract of recipients. This implies that it is over-attenuated and under extreme selection pressure. A less attenuated virus having the base U at position 472 and the base A at position 537 may therefore be more stable in the gut and take more effectively. However, it requires two simultaneous mutations to revert to wild-type and should thus be more stable than the Sabin strain. It may thus paradoxically be safer although less attenuated.

Our findings can be extrapolated to all polioviruses. Mutations at sites of type 1 and type 2 polioviruses corresponding to positions 472 and 537 of the 5' non-coding region of the genome of poliovirus type 3 Leon strain can lead to attenuation. There is a relatively high degree of homology between the genome RNA of the three types of poliovirus. The positions of another strain of poliovirus corresponding to positions 472 and 537 of poliovirus type 3 Leon strain can be determined by lining up the sequences of the genomic RNA of the strains. This has been done for the Sabin strains of each type of poliovirus in Toyoda et al, 1984, *J. Mol. Biol.* 174:561–585.

Accordingly the invention provides an attenuated poliovirus in which the 5' non-coding region of the genome is:

(a) the 5' non-coding region of poliovirus type 3 Leon strain modified by the provision of the bases uracil and adenine at positions 472 and 537 thereof respectively, or (b) the 5' non-coding region of another poliovirus modified by the provision of the bases uracil and adenine at respective positions corresponding to positions 472 and 537 of the 5' non-coding region of poliovirus type 3 Leon strain.

Such an attenuated poliovirus may therefore have the 5' non-coding region of a virulent or, indeed, of a non-virulent poliovirus except for the provision of the bases U and A at the appropriate positions. Apart from the provision of the bases U and A, the 5' non-coding region may be identical to that of a wild-type strain such as type 1 Mahoney strain or type 3 Leon strain or of a vaccine strain such as a Sabin strain.

The attenuated poliovirus may be a type 1, type 2 or type 3 poliovirus. Types 2 and 3 are preferred. For types 1 and 2, positions 469 and 534 correspond to positions 472 and 537 respectively of poliovirus type 3. The numbering system of the positions of the 5' non-coding region of poliovirus type 3, in particular of poliovirus type 3 Leon strain, is the numbering system employed in the Stanway et al paper above.

Any strain of poliovirus may be attenuated according to the present invention. An attenuated strain of type 3 poliovirus has the bases U and A at positions 472 and 537 respectively of the genome. An attenuated strain of type 1 or type 2 poliovirus has the bases U and A at the positions of the genome which correspond to positions 472 and 537 of the genome of poliovirus type 3 Leon strain. The genome of such attenuated strains may otherwise be identical to, for example, the genome of a vaccine strain such as a Sabin strain or of a wild-type strain such as type 1 Mahoney strain or type 3 Leon strain.

An attenuated virus according to the invention is prepared by a process comprising:

(i) sub-cloning a portion of a cDNA of a poliovirus, which portion includes the said positions 472 and 537 or the said corresponding positions;

(ii) mutating the said positions 472 and 537 or the said corresponding positions to uracil and adenine respectively in the sub-cloned portion;

(iii) reintroducing the thus mutated portion or a fragment thereof which includes the mutated positions into the complete cDNA from which the portion was derived; and (iv) obtaining live virus from the cDNA thus obtained.

A mutation can be introduced into a strain of a poliovirus, for example an existing vaccine strain of virus or a virulent strain such as wild-type virus, by site-directed mutagenesis. This may be achieved beginning with sub-cloning the appropriate region from an infectious DNA copy of the genome of any of the virus strain, for example a vaccine strain or its progenitor, into the single strand DNA of a bacteriophage such as M13. The virus strain may be a neurovirulent strain but is preferably a vaccine strain. For poliovirus it may be a Sabin, type 3 Leon or type 1 Mahoney strain. The desired mutation is then introduced into this sub-cloned cDNA using the technique of oligonucleotide directed mutagenesis.

After the introduction of mutation, the modified sub-cloned cDNAs are reintroduced into the complete cDNA from which they were derived and, for virulence testing in mice, into a cDNA derived from a murine poliovirus derivative known to cause a poliomyelitis type disease in mice (La Monica et al, 1986). Live virus is recovered from the mutated full length cDNA by production of a positive sense RNA typically using a T7 promoter to direct transcription in vitro (Van der Werf et al, 1986, *Proc NatlAcad Sci*, USA 83: 2330–2334). The recovered RNA may be applied to tissue cultures using standard techniques (Koch, 1973, *Curr Top Microbiol Immunol* 61: 89–138). After 4–6 days incubation virus can be recovered from the supernatant of the tissue culture. The level of neurovirulence of the modified virus may then be compared with that of the unmodified virus using a standard LD50 test in mice (La Monica et al, 1986) or the WHO approved vaccine safety test in monkeys (*WHO Tech Rep Ser* 687: 107–175, 1983).

The attenuated viruses can be used as vaccines. They may therefore be formulated as pharmaceutical compositions further comprising a pharmaceutically acceptable carrier or diluent. Any carrier or diluent conventionally used in vaccine preparations may be employed. For example, the presently used live attenuated poliovirus strains are stabilised in a solution of 1 molar $MgCl_2$ and administered as a mixture of the three serotypes.

The attenuated viruses can therefore be used to prevent an infection attributable to a poliovirus in a human patient. For this purpose, they may be administered orally, as a nasal spray, or parenterally, for example by subcutaneous or intramuscular injection. A dose corresponding to the amount administered for a conventional live virus vaccine, such as up to $10^6$ $TCID_{50}$ for a Sabin vaccine strain in the case of poliovirus, may be administered.

The following Example illustrates the invention.

EXAMPLE

Construction and characterisation of poliovirus type 3 (P3) 472/537 UA mutant.

This mutant was constructed in the Leon/Lansing hybrid genomic background (La Monica et al (1987), J. Virol. 61, 2917) by mutagenesis of pT7SFP (Skinner et al (1989), J. Mol. Biol. 207, 379; EP-A-0383433). A Pst I/SstI fragment of P3/Leon cDNA from nucleotide (nt) 1 to 751 was sub-cloned into M13 mp19 and mutagenised using the Mutagene kit (Biorad) and the following primers:

5'CCATGGTTAGAATTAGCCGCA3'(SEQ.ID.NO:1) and
5'GTAGTCGGTTTCGCCACGGAC3'(SEQ.ID.NO:2).

After verification of the sequence changes in the mutant phage a MluI/SstI fragment (nt 278 to 751) was reintegrated into pT7SFP. Recombinant DNA was cleaved with Sal I prior to RNA transcription and transfection of $HE_p2c$ cells. Recovered viruses were sequenced through the region 450–550 to verify changes at the viral RNA level. The 5' non-coding region of the mutant poliovirus was composed of the 5' non-coding region of the genome of poliovirus type 3 Leon strain except for the bases U and A at positions 472 and 537.

Plaque-assays in BGMs, at cell line derived from African Green Monkey kidney, at elevated temperatures (Macadam et al, Virology, 181, 451) showed that a 472/537 UA mutants was intermediate between UG (P3/Sabin-like) and CG (P3/Leon-like) mutants in temperature-sensitivity. The results are shown in the Table below. Results of neurovirulence assays in C57B16 mice suggested that UA mutants were also intermediate in virulence between UG and CG mutants. In that case, mice were inoculated by the intracranial route and observed for signs of paralysis for 22 days.

TABLE

| bases at positions 472 and 537 | temperature (T) at which $log_{10}$ (titre 35° C./titre T) = 1 |
|---|---|
| (1) C G | 39.4 |
| (2) G C | 39.3 |
| (3) U A | 39.1 |
| (4) U G | 38.7 |

We claim:

1. An attenuated vaccine strain of poliovirus in which the 5' non-coding region of the genome is modified by the provision of the bases uracil and adenine at respective positions corresponding to positions 472 and 537 of the 5' non-coding region of poliovirus type 3 Leon strain.

2. An attenuated virus according to claim 1, in which the vaccine strain is a Sabin strain.

3. An attenuated vaccine strain according to claim 1, which is a type 1 poliovirus.

4. An attenuated vaccine strain according to claim 1, which is a type 2 poliovirus.

5. An attenuated vaccine strain according to claim 1, which is a type 3 poliovirus.

6. A vaccine comprising a pharmaceutically acceptable carrier or diluent and an attenuated vaccine strain of poliovirus in which the 5' non-coding region of the genome is modified by the provision of the bases uracil and adenine at respective positions corresponding to positions 472 and 537 of the 5' non-coding region of poliovirus type 3 Leon strain.

7. A vaccine according to claim 6, in which the attenuated vaccine strain is a Sabin strain.

8. A vaccine according to claim 6, in which the attenuated vaccine strain is a type 1 poliovirus.

9. A vaccine according to claim 6, in which the attenuated vaccine strain is a type 2 poliovirus.

10. A vaccine according to claim 6, in which the attenuated vaccine strain is a type 3 poliovirus.

11. A method of vaccinating a patient against a poliovirus, which method comprises administering thereto an effective amount of an attenuated vaccine strain of poliovirus in which the 5' non-coding region of the genome is modified by the provision of the bases uracil and adenine at respective positions corresponding to positions 472 and 537 of the 5' non-coding region of poliovirus type 3 Leon strain.

12. A method according to claim 11, in which the attenuated vaccine strain is a Sabin strain.

13. A method according to claim 11, in which the attenuated vaccine strain is a type 1 poliovirus.

14. A method according to claim 11, in which the attenuated vaccine strain is a type 2 poliovirus.

15. A method according to claim 11, in which the attenuated vaccine strain is a type 3 poliovirus.

16. An attenuated poliovirus in which the 5' non-coding region of the genome is:

(a) the 5' non-coding region of poliovirus type 3 Leon strain modified by the provision of the bases uracil and adenine at positions 472 and 537 thereof respectively, or (b) the 5' non-coding region of another poliovirus modified by the provision of the bases uracil and adenine at respective positions corresponding to positions 472 and 537 of the 5' non-coding region of poliovirus type 3 Leon strain.

17. An attenuated poliovirus according to claim 16, which is a type 1 poliovirus.

18. An attenuated poliovirus according to claim 16, which is a type 2 poliovirus.

19. An attenuated poliovirus according to claim 16, which is a type 3 poliovirus.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

CCATGGTTAG AATTAGCCGC A                    21

( 2 ) INFORMATION FOR SEQ ID NO:2:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

GTAGTCGGTT TCGCCACGGA C                    21